United States Patent
Nuccio et al.

(10) Patent No.: US 8,304,607 B2
(45) Date of Patent: Nov. 6, 2012

(54) EPIDERMAL TISSUE PROMOTER DERIVED FROM POTATO FOR MONOCOTS

(75) Inventors: Michael Nuccio, Durham, NC (US); A. Todd Richmond, Durham, NC (US)

(73) Assignee: Syngenta Participations AG, Basel (CH)

( * ) Notice: Subject to any disclaimer, the term of this patent is extended or adjusted under 35 U.S.C. 154(b) by 331 days.

(21) Appl. No.: 12/643,187

(22) Filed: Dec. 21, 2009

(65) Prior Publication Data

US 2010/0138955 A1 Jun. 3, 2010

Related U.S. Application Data

(63) Continuation-in-part of application No. 11/109,594, filed on Apr. 19, 2005, now Pat. No. 8,129,588.

(60) Provisional application No. 60/563,687, filed on Apr. 20, 2004, provisional application No. 60/563,678, filed on Apr. 20, 2004.

(51) Int. Cl.
    *C12N 15/82* (2006.01)
    *A01H 5/00* (2006.01)
    *A01H 5/10* (2006.01)
(52) U.S. Cl. ............. 800/287; 536/24.1; 435/320.1; 435/419; 435/468; 800/298; 800/320.1
(58) Field of Classification Search ............ None
    See application file for complete search history.

(56) References Cited

U.S. PATENT DOCUMENTS

| | | | |
|---|---|---|---|
| 5,593,874 | A | 1/1997 | Brown et al. |
| 5,753,475 | A | 5/1998 | Houck |
| 6,140,554 | A | 10/2000 | O'Reilly et al. |
| 6,228,645 | B1 | 5/2001 | Bruce et al. |
| 6,239,329 | B1 | 5/2001 | Weigel et al. |
| 6,342,657 | B1 | 1/2002 | Thomas et al. |
| 2003/0106106 | A1 | 6/2003 | Takakura et al. |
| 2004/0045053 | A1 | 3/2004 | Greenland et al. |

OTHER PUBLICATIONS

Ancillo G. et al. The promoter of the potato chitinase C gene directs expression to epidermal cells. Planta. Aug. 2003;217(4):566-76. Epub May 6, 2003.*
Raboy V. et al. Origin and seed phenotype of maize low phytic acid 1-1 and low phytic acid 2-1. Plant Physiol. Sep. 2000;124(1):355-68.*
Larkin et al., The Plant Cell, 1993, 5, pp. 1739-1748.
Sieburth et al., Plant Cell, 1997, 9, 3, pp. 355-365.
Ishida et al., Nat Biotechnol., 1996, 14, 6, pp. 745-750.
Callis et al., Genes and Development, 1987, 1, pp. 1183-1200.
Wilkie et al., Trends Biochem Sci., 2003, 28, 4, pp. 182-188.
Aoki et al., Plant Cell Physiol., 1999, 40, 10, pp. 1072-1078.
GenBank: AF153195.1, *Solanum tuberosum* class 1 chitinase (ChtC2) gene, complete cds, downloaded from the Internet on Feb. 16, 2010, http://www.ncbi.nlm.gov/nuccore/6707112?report.

* cited by examiner

*Primary Examiner* — Cynthia Collins
(74) *Attorney, Agent, or Firm* — Bruce Vrana (57) ABSTRACT

The presently disclosed subject matter includes nucleic acid sequences and expression cassettes that contain regulatory sequences derived from *Solanum tuberosum* chitinase C genes, for expression of recombinant gene products in plants. The expression cassette drives high transgene expression in the epidermal (L1) cell layer.

14 Claims, 1 Drawing Sheet

EPIDERMAL TISSUE PROMOTER DERIVED FROM POTATO FOR MONOCOTS

CROSS-REFERENCE TO RELATED APPLICATIONS

This application is a continuation-in-part of U.S. application Ser. No. 11/109,594, filed May 18, 2005, which claims priority to U.S. Provisional Application Nos. 60/563,687, filed Apr. 20, 2004, and 60/563,678, filed Apr. 20, 2004. These applications are herein incorporated by reference in their entirety.

TECHNICAL FIELD

The presently disclosed subject matter includes expression cassettes that contain regulatory sequences derived from a target gene, for example, regulatory sequences from the potato chitinase C gene, for tissue specific expression of recombinant gene products in plants.

BACKGROUND

In agricultural biotechnology, plants can be modified according to one's needs. One way to accomplish this is by using modern genetic engineering techniques. For example, by introducing a gene of interest into a plant, the plant can be specifically modified to express a desirable phenotypic trait. For this, plants are transformed most commonly with a heterologous gene comprising a promoter region, a coding region and a termination region. When genetically engineering a heterologous gene for expression in plants, the selection of a promoter is often a factor. While it can be desirable to express certain genes constitutively, i.e. throughout the plant at all times and in most tissues and organs, other genes are more desirably expressed only in response to particular stimuli or confined to specific cells or tissues.

It has been shown that certain promoters are able to direct RNA synthesis at a higher rate than others. These are called "strong promoters". Certain other promoters have been shown to direct RNA synthesis at higher levels only in particular types of cells or tissues and are often referred to as "tissue specific promoters", or "tissue-preferred promoters", if the promoters direct RNA synthesis preferentially in certain tissues (RNA synthesis can occur in other tissues at reduced levels). Since patterns of expression of a nucleotide sequence of interest introduced into a plant, plant tissue or plant cell are controlled using promoters, there is an ongoing interest in the isolation of novel promoters that are capable of controlling the expression of a nucleotide sequence of interest at certain levels in specific tissue types or at specific plant developmental stages.

Furthermore, this document incorporates herein by reference US Patent Application Publication No: 2007/006344, Ser. No. 11/109,594 in its entirety.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments, it is the object of the presently disclosed subject matter to provide an isolated nucleic acid sequence comprising SEQ ID NO: 1 or a functional fragment thereof. In some embodiments, provided is an isolated nucleic acid sequence at least 90% identical to SEQ ID NO: 1.

In some embodiments, the presently disclosed subject matter includes an isolated nucleic acid molecule capable of hybridizing under highly stringent conditions to a nucleic acid sequence fully complementary to SEQ ID NO: 1.

In some embodiments, the presently disclosed subject matter also relates to an expression cassette comprising a promoter comprising SEQ ID NO: 1, or a functional fragment thereof, operably linked to a heterologous gene. In some embodiments, the expression cassette further comprises a prokaryotic gene regulatory sequence. In some embodiments, the expression cassette further comprises SEQ ID NO: 2 (a terminator sequence)

In some embodiments, the heterologous gene of the expression cassette is a gene for resistance to herbicides, pests, disease, or drought.

In some embodiments, the presently disclosed subject matter also relates to a plant, plant cell, plant tissue, or portion thereof comprising an expression cassette comprising a promoter comprising SEQ ID NO: 1. The presently disclosed subject matter further relates to the plant, plant tissue, or plant cell, or portion thereof comprising the expression cassette, wherein the plant, plant tissue, or plant cell, or portion thereof is a monocot. In some embodiments, the presently disclosed subject matter further relates to the plant, plant tissue, or plant cell, or portion thereof comprising the expression cassette, wherein the plant, plant tissue, or plant cell, or portion thereof is maize.

In some embodiments, the presently disclosed subject matter relates to a method of expressing a heterologous gene comprising: (a) providing an expression cassette comprising a promoter comprising SEQ ID NO: 1, operably linked to a heterologous gene, wherein the expression cassette is functional in a plant, plant tissue, or plant cell, or portion thereof; and (b) creating a plant, plant tissue, or plant cell, or portion thereof comprising the expression cassette, wherein the heterologous gene is expressed. The presently disclosed subject matter further relates to expressing the heterologous gene in a plant, plant tissue, plant cell, or portion thereof wherein the plant, plant tissue, or plant cell, or portion thereof is a monocot. The presently disclosed subject matter further relates to expressing the heterologous gene in a plant, plant tissue, or plant cell, or portion thereof wherein the plant, plant tissue, or plant cell, or portion thereof is maize. In some embodiments, the presently disclosed subject matter further relates to expressing the heterologous gene in an epidermal cell layer of aerial plant tissue.

In some embodiments, the presently disclosed subject matter relates to a plant, plant tissue, plant cell, or portion thereof made by the following method: (a) providing an expression cassette comprising SEQ ID NO: 1, wherein the expression cassette is functional in a plant, plant tissue, or plant cell, or portion thereof; and (b) creating a plant, plant tissue, plant cell, or portion thereof comprising the expression cassette, wherein the heterologous gene is expressed. The presently disclosed subject matter further relates to progeny, seed, or grain produced by the plant, plant tissue, plant cell, or portion thereof described above, wherein the progeny retain SEQ ID NO: 1 operably linked to a nucleotide sequence of interest.

In some embodiments, the presently disclosed subject matter relates to an expression cassette comprising a 5'-regulatory sequence and a nucleic acid molecule operably linked to said 5'-regulatory sequence, wherein said nucleic acid molecule is heterologous to the 5'-regulatory sequence, and wherein the product of the expression of said nucleic acid molecule is targeted to the epidermal tissue of a plant. The 5'-regulatory sequence comprises the following regions of a potato chitinase C gene derived from *Solanum tuberosum*: a promoter, a first exon, a first intron, and a 5' portion of a second exon, wherein said 5'-regulatory sequence has been engineered to include a translational initiation codon at the 3' end of said 5'-regulatory sequence, and not to contain additional translation initiation codons upstream of said translation initiation codon. The presently disclosed subject matter further relates to an expression cassette wherein the 5' portion of the second exon comprises the first 15 nucleotides from the 5' end of the exon and a Kozak sequence.

As a result of the presently disclosed subject matter having been stated hereinabove, and which is achieved in whole or in part by the presently disclosed subject matter, other objects will become evident as the description proceeds when taken in connection with the accompanying Examples and FIGURE as best described herein below.

BRIEF DESCRIPTION OF THE SEQUENCES IN THE SEQUENCE LISTING

SEQ ID NO: 1 is the nucleotide sequence of the StChiC promoter.

SEQ ID NO: 2 is the nucleotide sequence of the StChiC terminator.

SEQ ID NO: 3 is the nucleotide sequence of the gDNA GenBank accession number AF153195.

SEQ ID NO: 4 is the nucleotide sequence of the cDNA GenBank accession number AF153195.

SEQ ID NO: 5 is the forward primer, STCHICP1 forw, used to clone the 5' regulatory sequence of STCHIC.

SEQ ID NO: 6 is the reverse primer, STCHICP2 rev, used to clone the 5' regulatory sequence of STCHIC.

SEQ ID NO: 7 is the nucleotide sequence of oligonucleotide prStChiCmut1.

SEQ ID NO: 8 is the nucleotide sequence of oligonucleotide prStChiCmut2.

SEQ ID NO: 9 is the nucleotide sequence of oligonucleotide prStChiCmut3.1.

SEQ ID NO: 10 is the nucleotide sequence of oligonucleotide prStChiCmut4.

SEQ ID NO: 11 is the nucleotide sequence of oligonucleotide prStChiCmut 5.1.

SEQ ID NO: 12 is the forward primer, STCHICT1 forw, used to clone the 3' regulatory sequence of STCHIC.

SEQ ID NO: 13 is the reverse primer, STCHICT2 rev, used to clone the 3' regulatory sequence of STCHIC.

SEQ ID NO: 14 is the nucleotide sequence of a 5'-non-transcribed sequence of the StChiC promoter.

SEQ ID NO: 15 is the nucleotide sequence of the first intron of the StChiC promoter.

SEQ ID NO: 16 is the nucleotide sequence of a 5'-UTR representing exon 1 of the StChiC promoter.

SEQ ID NO: 17 is the nucleotide sequence of a 5'-UTR representing partial exon 2 of the StChiC promoter.

SEQ ID NO: 18 is the nucleotide sequence of a 3'-UTR of the StChiC terminator.

SEQ ID NO: 19 is the nucleotide sequence of a 3'-non-transcribed region of the StChiC terminator.

SEQ ID NO: 20 is the nucleotide sequence of exon 2 of StChiC.

DEFINITIONS

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. For example, the phrase "a marker" refers to one or more markers. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to whole number values between 1 and 100 and greater than 100.

Unless otherwise indicated, all numbers expressing quantities of ingredients, reaction conditions, and so forth used in the specification and claims are to be understood as being modified in all instances by the term "about". The term "about", as used herein when referring to a measurable value such as an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods. Accordingly, unless indicated to the contrary, the numerical parameters set forth in this specification and attached claims are approximations that can vary depending upon the desired properties sought to be obtained by the presently disclosed subject matter.

As used herein, the term "and/or" when used in the context of a list of entities, refers to the entities being present singly or in combination. Thus, for example, the phrase "A, B, C, and/or D" includes A, B, C, and D individually, but also includes any and all combinations of A, B, C, and D.

The term "comprising", which is synonymous with "including" "containing", or "characterized by", is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, or ingredient not specifically recited. For example, when the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter.

With respect to the terms "comprising", "consisting essentially of", and "consisting of", where one of these three terms is used herein, the presently disclosed and claimed subject matter can include the use of either of the other two terms.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

The term "abiotic stress" refers to nonliving environmental factors such as frost, drought, excessive heat, high winds, etc., that can have harmful effects on plants.

The term "nucleic acid" refers to a polynucleotide of high molecular weight which can be single-stranded or double-stranded, composed of monomers (nucleotides) containing a sugar, phosphate and a base which is either a purine or pyrimidine. A "nucleic acid fragment" is a fraction of a given nucleic acid molecule. In higher plants, deoxyribonucleic acid (DNA) is the genetic material while ribonucleic acid (RNA) is involved in the transfer of information contained within DNA into proteins. A "genome" is the entire body of genetic material contained in each cell of an organism. The term "nucleotide sequence" refers to a polymer of DNA or RNA which can be single- or double-stranded, optionally containing synthetic, non-natural or altered nucleotide bases capable of incorporation into DNA or RNA polymers. Unless otherwise indicated, a particular nucleic acid sequence of the presently disclosed subject matter also implicitly encompasses conservatively modified variants thereof (e.g. degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer, et al., Nucleic Acid Res. 19:5081 (1991); Ohtsuka, et al., J. Biol. Chem. 260:2605-2608 (1985); and Rossolini, et al., Mol. Cell. Probes 8:91-98 (1994)). The term nucleic acid is used interchangeably with gene, cDNA, and mRNA encoded by a gene.

"Operably-linked" refers to the association of nucleic acid sequences on a single nucleic acid fragment so that the function of one is affected by the other. For example, a promoter is operably-linked with a coding sequence or functional RNA when it is capable of affecting the expression of that coding sequence or functional RNA (i.e., that the coding sequence or functional RNA is under the transcriptional control of the promoter). Coding sequences in sense or antisense orientation can be operably-linked to regulatory sequences.

"Promoter" refers to a nucleotide sequence, which controls the expression of a coding sequence by providing the recognition for RNA polymerase and other factors required for proper transcription. "Promoter regulatory sequences" can comprise proximal and more distal upstream elements and/or downstream elements. Promoter regulatory sequences influence the transcription, RNA processing or stability, or translation of the associated coding sequence. Regulatory sequences include enhancers, untranslated leader sequences, introns, exons, and polyadenylation signal sequences. They include natural and synthetic sequences as well as sequences that can be a combination of synthetic and natural sequences. An "enhancer" is a nucleotide sequence that can stimulate promoter activity and can be an innate element of the promoter or a heterologous element inserted to enhance the level or tissue specificity of a promoter. The primary sequence can be present on either strand of a double-stranded DNA molecule, and is capable of functioning even when placed either upstream or downstream from the promoter. The meaning of the term "promoter" includes "promoter regulatory sequences."

"Primary transformant" and "T0 generation" refer to transgenic plants that are of the same genetic generation as the tissue that was initially transformed (i.e., not having gone through meiosis and fertilization since transformation). "Secondary transformants" and the "T1, T2, T3, etc. generations" refer to transgenic plants derived from primary transformants through one or more meiotic and fertilization cycles. They can be derived by self-fertilization of primary or secondary transformants or crosses of primary or secondary transformants with other transformed or untransformed plants.

"Transgenic event" and "event" refer to the successful incorporation of a nucleotide sequence in a cell. The unique recombination of DNA that occurs in one cell can be used to generate an entire transgenic plant. Events can be introduced into other cultivars by breeding.

"Gene" refers to a nucleic acid fragment that expresses mRNA, functional RNA, or specific protein, including regulatory sequences. The term "native gene" refers to a gene as found in nature. The term "chimeric gene" refers to any gene that contains 1) DNA sequences that are not found together in nature, or 2) sequences encoding parts of proteins not naturally adjoined. A "transgene" can refer to a gene that has been introduced into the genome by transformation and in some embodiments is stably maintained. Transgenes can include, for example, genes that are either heterologous or homologous to the genes of a particular plant to be transformed. Additionally, transgenes can comprise unmodified genes inserted into an organism. Transgenes can be chimeric genes.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but can also code for a functional RNA of interest, for example antisense RNA or a nontranslated RNA, in the sense or antisense direction. The expression cassette comprising the nucleotide sequence of interest can be chimeric, meaning that at least one of its components is heterologous with respect to at least one of its other components.

"Intron" refers to an intervening section of DNA that occurs almost exclusively within a eukaryotic gene, but which is not translated to amino acid sequences in the gene product. The introns are removed from the pre-mature mRNA through a process called splicing, which joins the exons to form an mRNA. For purposes of the presently disclosed subject matter, the definition of the term "intron" includes modifications to the nucleotide sequence of an intron derived from a target gene.

"Exon" refers to a section of DNA that carries the coding sequence for a protein or part of it. Exons are separated by intervening, non-coding sequences (introns). For purposes of the presently disclosed subject matter, the definition of the term "exon" includes modifications to the nucleotide sequence of an exon derived from a target gene.

Expression or overexpression of a gene involves transcription of the gene and translation of the mRNA into a precursor or mature protein. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression or transcript accumulation of identical or substantially similar foreign or endogenous genes. The mechanism of co-suppression can be at the DNA level (such as DNA methylation), at the transcriptional level, or at post-transcriptional level.

The term "constitutive promoter" refers to a promoter active in all or most tissues of a plant at all or most developmental stages. As with other promoters classified as constitutive, some variation in absolute levels of expression can exist among different tissues or stages.

An "isolated nucleic acid fragment" refers to a polymer of ribonucleotides (RNA) or deoxyribonucleotides (DNA) that is single- or double-stranded, optionally containing synthetic, non-natural or altered nucleotide bases. An isolated nucleic acid fragment in the form of DNA can be comprised of one or more segments of cDNA, genomic DNA or synthetic DNA.

The terms "polynucleotide", "polynucleotide sequence", "nucleic acid sequence", "nucleotide sequence", and "nucleic acid fragment"/"isolated nucleic acid fragment" are used interchangeably herein. A polynucleotide can be a polymer of RNA or DNA that is single- or double-stranded, that optionally contains synthetic, non-natural or altered nucleotide bases. A polynucleotide in the form of a polymer of DNA can be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A "heterologous nucleic acid fragment" refers to a sequence that is not naturally occurring with the plant promoter sequence of the invention. While this nucleotide sequence is heterologous with respect to the promoter sequence, it can be homologous, or native, or heterologous, or foreign, to the plant host.

The term "substantially similar" as used herein refer to nucleic acid fragments wherein changes in one or more nucleotide bases do not affect the ability of the nucleic acid fragment to mediate gene expression or produce a certain phenotype. These term also refer to modifications of the nucleic acid fragments of the presently disclosed subject matter such as deletion or insertion of one or more nucleotides that do not substantially alter the functional properties of the resulting nucleic acid fragment relative to the initial, unmodified fragment. It is therefore understood, as those skilled in the art will appreciate, that the presently disclosed subject matter encompasses more than the specific exemplary sequences.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., Plant Cell 1:671-680 (1989).

"Transformation" refers to the transfer of a nucleic acid fragment into the genome of a host organism, resulting in genetically stable inheritance. Host organisms containing the transformed nucleic acid fragments are referred to as "transgenic" organisms.

"Transient expression" refers to the temporary expression of often reporter genes such as β-glucuronidase (GUS), fluorescent protein genes GFP, ZS-YELLOW1 N1, AM-CYAN1, DS-RED in selected certain cell types of the host organism in which the transgenic gene is introduced temporally by a transformation method. Transient expression of a gene refers to the expression of a gene that is not integrated into the host chromosome but functions independently, either as part of an autonomously replicating plasmid or expression cassette, for example, or as part of another biological system such as a virus. "Transiently transformed" refers to cells in which transgenes and foreign DNA have been introduced (for example, by such methods as *Agrobacterium*-mediated transformation or biolistic bombardment). Transient expression assay protocols are well known in the art, and include Sessa, et al. (Sessa G, Borello U, Morelli G, Ruberti I. 1998. A Transient Assay for Rapid Functional Analysis of Transcription Factors in Arabidopsis. Plant Molecular Biology Reporter. 16:191-197) and Mitsui, et at (Mitsui M, Murohashi Y, Asano Y, Masada M, Kodama H. 2003. Transient Assay for in vivo Splicing in Tobacco Leaf Cells by Particle Bombardment. Plant Molecular Biology Reporter. 21:21-30).

Standard recombinant DNA and molecular cloning techniques used herein are well known in the art and are described more fully in Sambrook, J. et al., In Molecular Cloning: A Laboratory Manual; $2^{nd}$ ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In Current Protocols in Molecular Biology; John Wiley and Sons: New York, 1990 (hereinafter "Ausubel et al., 1990").

"PCR" or "Polymerase Chain Reaction" is a technique for the synthesis of large quantities of specific DNA segments, including a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps comprises a cycle.

As used herein, the phrase "TAQMAN® Assay" refers to real-time sequence detection using PCR based on the TAQMAN® Assay sold by Applied Biosystems, Inc. of Foster City, Calif., United States of America.

As used herein, the phrase "stringent hybridization conditions" refers to conditions under which a polynucleotide hybridizes to its target subsequence, typically in a complex mixture of nucleic acids, but to essentially no other sequences. Stringent conditions are sequence-dependent and can be different under different circumstances. Longer sequences typically hybridize specifically at higher temperatures. An extensive guide to the hybridization of nucleic acids is found in Tijssen, 1993. Generally, stringent conditions are selected to be about 5-10° C. lower than the thermal melting point (Tm) for the specific sequence at a defined ionic strength and pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Exemplary stringent hybridization is performed at a temperature of 65° C., preferably 60° C. and most preferably 55° C. in double strength (2×) citrate buffered saline (SSC) containing 0.1% SDS followed by rinsing of the support at the same temperature but with a buffer having a reduced SSC concentration. Such reduced concentration buffers are typically one tenth strength SSC (0.1×SSC) containing 0.1% SDS, preferably 0.2×SSC containing 0.1% SSC and most preferably half strength SSC (0.5×SSC) containing 0.1% SDS.

Additional guidelines for determining hybridization parameters are provided in numerous references (see e.g., Ausubel et al., 1999).

General Considerations

Promoters can comprise several regions that play a role in function of the promoter. Some of these regions are modular, in other words they can be used in isolation to confer promoter activity or they can be assembled with other elements to construct new promoters. The first of these promoter regions lies immediately upstream of the coding sequence and forms the "core promoter region" containing consensus sequences, normally 20-70 base pairs immediately upstream of the coding sequence. The core promoter region typically contains a TATA box and often an initiator element as well as the initiation site. The precise length of the core promoter region is not fixed but is usually well recognizable. Such a region is normally present, with some variation, in most promoters. The core promoter region is often referred to as a minimal promoter region because it is functional on its own to promote a basal level of transcription.

The presence of the core promoter region defines a sequence as being a promoter: if the region is absent, the promoter is non-functional. The core region acts to attract the general transcription machinery to the promoter for transcription initiation. However, the core promoter region is typically not sufficient to provide promoter activity at a desired level. A series of regulatory sequences, often upstream of the core, constitute the remainder of the promoter. The regulatory sequences can determine expression level, the spatial and temporal pattern of expression and, for a subset of promoters, expression under inductive conditions (regulation by external factors such as light, temperature, chemicals and hormones). Regulatory sequences can be short regions of DNA sequence 6-100 base pairs that define the binding sites for trans-acting factors, such as transcription factors. Regulatory sequences can also be enhancers, longer regions of DNA sequence that can act from a distance from the core promoter region, sometimes over several kilobases from the core region. Regulatory sequence activity can be influenced by trans-acting factors including but not limited to general transcription machinery, transcription factors and chromatin assembly factors.

DETAILED DESCRIPTION

In some embodiments an expression cassette of the presently disclosed subject matter is based on a potato gene, namely the potato chitinase C (StChiC) gene, which is characterized as being specifically expressed in the epidermal cell layer of aerial tissue. The StChiC gene's promoter (1322 bp of 5'-sequence upstream of the transcription start site) was previously shown to drive reporter gene expression in transient and stable transformation experiments with potato, a dicot (Ancillo et al., 2003). The presently disclosed subject matter adapts this technology for use in monocots, such as maize.

Though it is not common to use dicot promoters in maize or any other monocot, there have been studies that report dicot promoters functioning correctly in monocots and vice versa (Koyama et al., 2005; Liu et al., 2003). In some embodiments the presently disclosed subject matter involves tailoring cassette performance to the transgene environment (plant chromatin). This enables robust trait expression using plant gene regulatory sequences only. However, an additional prokaryotic gene regulatory sequence can be included in the expression cassette as an option.

In some embodiments the expression cassette comprises a 5'-regulatory sequence containing the promoter linked to the first exon, first intron and part of the second exon of the StChiC gene. The natural translation start codon and downstream ATG codons were disrupted to ensure translation from this transcript begins at an engineered translation start codon on the second exon. In some embodiments, the presently disclosed subject matter provides a novel isolated nucleic acid sequence comprising SEQ ID NO: 1.

In some embodiments, the presently disclosed subject matter provides an expression cassette comprising SEQ ID NO: 1 operably linked to a heterologous gene. In one aspect the expression cassette comprises a 5'-regulatory sequence and a nucleic acid molecule operably linked to the 5'-regulatory sequence, wherein the nucleic acid molecule is heterologous to the 5'-regulatory sequence. The 5'-regulatory sequence can comprise the following regions of a potato chitinase C gene obtained from *Solanum tuberosum*: a promoter, a first exon, a first intron, and a 5' portion of a second exon. The 5'-regulatory sequence is engineered to include a translational initiation codon at its 3' end, and not to contain additional translation initiation codons upstream of the translation initiation codon. The term "portion" as used here can refer to a sequence from an intron or exon, such as from the 5' end of exon 2, of a desired length as can be determined by the guidance provided herein including the Examples herein below. By way of example and not limitation, the 5' portion of the second exon included in the cassette can include the first 15 nucleotides from the 5' end of the exon. The product of the expression of the nucleic acid molecule can be targeted to the epidermal tissue of a plant. The expression cassette design is first disclosed in U.S. Publication No. 2007/0006344, which is incorporated herein by reference.

In some embodiments, the presently disclosed subject matter provides for a method of making an expression cassette comprising SEQ ID NO: 1 operably linked to a heterologous gene. In one aspect the expression cassette comprises a 5'-regulatory sequence and a nucleic acid molecule operably linked to the 5'-regulatory sequence, wherein the nucleic acid molecule is heterologous to the 5'-regulatory sequence. The 5'-regulatory sequence can comprise the following regions of a potato chitinase C gene obtained from *Solanum tuberosum*: a promoter, a first exon, a first intron, and a 5' portion of a second exon. The 5'-regulatory sequence is engineered to include a translational initiation codon at its 3' end, and not to contain additional translation initiation codons upstream of the translation initiation codon. The term "portion" as used here can refer to a sequence from an intron or exon, such as from the 5' end of exon 2, of a desired length as can be determined by the guidance provided herein including the Examples herein below. By way of example and not limitation, the 5' portion of the second exon included in the cassette can include the first 15 nucleotides from the 5' end of the exon.

The product of the expression of the nucleic acid molecule can be targeted to the epidermal tissue of a plant.

In some embodiments, the expression cassette also comprises a terminator (SEQ ID NO: 2) based on the same potato chitinase C gene. The terminator initiates just 3'- of the translation stop codon and extends 637 bases downstream. It includes 3'-untranslated sequence as well as 3'-non-transcribed sequence. The terminator is designed to function as a polyadenylation signal and a transcription stop signal. This design strategy is useful for the development of plant genetic engineering components.

The presently disclosed subject matter can be used to express traits that influence gas exchange in maize. These include, but are not limited to, traits that increase the cell's sensitivity to abscisic acid (ABA), traits that influence environmental signal transduction and other traits that can improve a plant's ability to tolerate abiotic stresses. The presently disclosed subject matter can provide for expression of a trait of interest in the epidermal cell layer of the plant. This can reduce or prevent deleterious effects on plant development. The presently disclosed subject matter can provide expression of heterologous products in plants. These changes can result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as understanding of agronomic characteristics and traits such as yield and heterosis increase, the choice of genes for transformation will change accordingly. Categories of transgenes, also known as heterologous genes, for example, include, but are not limited to, genes encoding important agronomic traits, insect resistance, disease resistance, herbicide resistance, sterility, grain or seed characteristics, and commercial products. Genes of interest include, generally, those involved in oil, starch, carbohydrate, or nutrient metabolism as well as those affecting seed size, plant development, plant growth regulation, and yield improvement. Plant development and growth regulation also refer to the development and growth regulation of various parts of a plant, such as the flower, seed, root, leaf, and shoot.

Other commercially desirable traits are genes and proteins conferring cold, heat, salt, and drought resistance. By way of example and not limitation, strategies to construct drought tolerant maize using genetic engineering technology require both a robust trait gene and accurate control of trait gene expression. Many drought tolerance trait genes redirect metabolic energy to survival mechanisms and therefore tend to carry a yield penalty. Effective deployment of these genes can depend on expression control. The trait gene should be active when and where it has the greatest positive effect and inactive everywhere else.

A representative drought trait for maize is the Yield Protection Technology (YPT)® technology offered by Performance Plants (Wang et al., 2005). This technology renders cells hypersensitive to the plant hormone abscisic acid (ABA). It is believed to be most effective in guard cells. It has been shown to work when coupled to a drought-inducible promoter (Wang et al., 2005). One strategy to effectively deploy the YPT™ trait is to direct its expression to the L1 or epidermal cell layer in aerial tissue.

Disease and/or insect resistance genes can encode resistance to pests that have great yield drag such as for example seed decay, seedling diseases, and bacterial blight. Genes conferring insect resistance include, for example, *Bacillus thuringiensis* toxic protein genes (U.S. Pat. Nos. 5,366,892; 5,747,450; 5,737,514; 5,723,756; 5,593,881; and Geiser et al (1986) Gene 48:109); lectins (Van Damme et al. (1994) Plant Mol. Biol. 24:825); and the like.

The promoter nucleotide sequences, expression cassettes, and methods disclosed herein are useful in regulating expression of any heterologous nucleic acid sequences in a host plant, which in some embodiments can alter the phenotype of a plant.

The presently disclosed subject matter includes the transformation of a recipient cell with at least one advantageous transgene. Two or more transgenes can be supplied in a single transformation event using either distinct transgene-encoding vectors, or a single vector incorporating two or more gene coding sequences. Any two or more transgenes of any description, such as those conferring herbicide, insect, disease (viral, bacterial, fungal, and nematode) or drought resistance, oil quantity and quality, or those increasing yield or nutritional quality can be employed as desired.

The isolated promoter sequence of the presently disclosed subject matter can be modified to provide a range of aerial epidermal or L1-specific expression levels of the heterologous nucleotide sequence. Thus, less than the entire promoter regions can be utilized and the ability to drive expression of the coding sequence retained. However, it is recognized that expression levels of the mRNA can be decreased with deletions of portions of the promoter sequences. Therefore, nucleic acid sequences, such as but not limited to fragments of SEQ ID NO: 1, which are 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 1 can still function as exemplified by this description. A functional fragment is a fragment that retains the capability to drive gene expression in a plant. Additional guidance as to the selection and modification of regions of SEQ ID NO: 1 can be found under the heading "GENERAL CONSIDERATIONS" herein above.

Optimal alignment of sequences for comparison for percent identity can be conducted by computerized implementations of known algorithms, or by visual inspection. Readily available sequence comparison and multiple sequence alignment algorithms are, respectively, the Basic Local Alignment Search Tool (BLAST) and ClustalW programs, both available on the internet. Other suitable programs include, but are not limited to, GAP, BestFit, Plot Similarity, and FASTA, which are part of the Accelrys GCG Package available from Accelrys, Inc. of San Diego, Calif., United States of America. In some embodiments, a percentage of sequence identity refers to sequence identity over the full length of one of the sequences being compared. In some embodiments, a calculation to determine a percentage of sequence identity does not include in the calculation any nucleotide positions in which either of the compared nucleic acids includes an "n" (i.e., where any nucleotide could be present at that position).

In some embodiments, the isolated nucleic acid sequence of the presently disclosed subject matter includes an isolated nucleic acid molecule capable of hybridizing, under highly stringent conditions, to a nucleic acid sequence fully complementary to SEQ ID NO: 1. A stringent hybridization is performed at a temperature of 65° C., preferably 60° C. and most preferably 55° C. in double strength (2×) citrate buffered saline (SSC) containing 0.1% SDS followed by rinsing of the support at the same temperature but with a buffer having a reduced SSC concentration. Such reduced concentration buffers are typically one tenth strength SSC (0.1×SSC) containing 0.1% SDS, preferably 0.2×SSC containing 0.1% SSC and most preferably half strength SSC (0.5×SSC) containing 0.1% SDS.

Plasmid vectors comprising the instant recombinant expression cassettes can be constructed. The choice of plasmid vector can be dependent upon the method that will be used to transform host cells. The skilled artisan is well aware of the genetic elements that must be present on the plasmid vector in order to successfully transform, select and propagate host cells containing the chimeric gene.

Methods for transforming monocots, primarily by use of *Agrobacterium tumefaciens* and by biolistic approaches, and obtaining transgenic plants have been published for monocots (U.S. Pat. No. 6,037,522), wheat (Cheng et al., Plant Cell Rep. 15:971-980 (1997), and in particular maize (U.S. Pat. No. 6,051,409).

There are a variety of methods for the regeneration of plants from plant tissues. The particular method of regeneration will depend on the starting plant tissue and the particular plant species to be regenerated. The regeneration, development and cultivation of plants from single plant protoplast transformants or from various transformed explants is well known in the art (Weissbach and Weissbach, Eds.; In Methods for Plant Molecular Biology; Academic Press, Inc.: San Diego, Calif., 1988). This regeneration and growth process typically includes the steps of selection of transformed cells, culturing those individualized cells through the usual stages of embryonic development or through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the presently disclosed subject matter containing a desired polypeptide is cultivated using methods well known to one skilled in the art.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant DNA fragments and recombinant expression constructs and the screening and isolating of clones, (see for example, Sambrook, J. et al., In Molecular Cloning: A Laboratory Manual; $2^{nd}$ ed.; Cold Spring Harbor Laboratory Press: Cold Spring Harbor, N.Y., 1989; Maliga et al., In Methods in Plant Molecular Biology; Cold Spring Harbor Press, 1995; Birren et al., In Genome Analysis: Detecting Genes, 1; Cold Spring Harbor: New York, 1998; Birren et al., In Genome Analysis: Analyzing DNA, 2; Cold Spring Harbor: New York, 1998; Clark, Ed., In Plant Molecular Biology: A Laboratory Manual; Springer: New York, 1997).

The skilled artisan will also recognize that different independent transformation events will result in different levels and patterns of expression of a transgenic nucleotide sequence (Jones et al., EMBO J. 4:2411-2418 (1985); De Almeida et al., Mol. Gen. Genetics 218:78-86 (1989)). Thus, multiple events must be screened in order to obtain lines displaying the desired expression level and pattern. Such screening can be accomplished by Northern analysis of mRNA expression, Western analysis of protein expression, in situ hybridization in isolated plant tissues or phenotypic analysis. Also of interest are seeds obtained from transformed plants displaying the desired gene expression profile.

Transformation and selection can be accomplished using methods well-known to those skilled in the art including, but not limited to, the methods described herein.

Thus the presently disclosed subject matter includes a plant, plant tissue, plant cell, or portion thereof comprising an expression cassette comprising a promoter comprising SEQ ID NO: 1. The presently disclosed subject matter further relates to the plant, plant tissue, plant cell, or portion thereof comprising the expression cassette, wherein the plant, plant cell, or plant tissue or portion thereof is a monocot. The monocot can be maize.

In some embodiments, the presently disclosed subject matter relates to a method of expressing a heterologous gene comprising first providing an expression cassette described above and creating a plant, plant tissue, or plant cell, or portion thereof comprising the expression cassette, wherein the heterologous gene is expressed. The expression cassette has a promoter comprising SEQ ID NO: 1 operably linked to a heterologous gene. The expression cassette is functional in a plant, plant tissue, plant cell, or portion thereof. The presently disclosed subject matter further relates to expressing the heterologous gene in a plant, plant tissue, plant cell, or portion thereof wherein the plant, plant tissue, or plant cell, or portion thereof is a monocot, including maize. The presently disclosed subject matter further relates to expressing the heterologous gene in an epidermal cell layer of aerial plant tissue.

The presently disclosed subject matter further relates to a plant, plant cell, or plant tissue or portion thereof made by the method of expressing a heterologous gene comprising (a) providing an expression cassette comprising SEQ ID NO: 1, wherein the expression cassette is functional in a plant, plant cell, or plant tissue or portion thereof; and (b) creating a plant, plant cell, or plant tissue or portion thereof comprising the expression cassette, wherein the heterologous gene is expressed. The presently disclosed subject matter further relates to expressing the heterologous gene in a plant, plant cell, or plant tissue or portion thereof wherein the plant, plant cell, or plant tissue or portion thereof is a monocot, including maize.

Transient expression provides a convenient, high-throughput, qualitative assay for functional variation in a protein of interest. The tissue specific expression vector described herein may be a transient expression vector that can transiently express heterologous genes in plants.

A further embodiment of the present invention includes preparing fragments of SEQ ID NO: 1 and testing for promoter activity by transient expression. Fragments of SEQ ID NO: 1 are prepared by cleaving one or more nucleotides from the promoter sequence by, including but not limited to, restriction enzyme digest, endonuclease digest, Klenow fragment digest, and by shearing. Fragments of SEQ ID NO: 1 hybridize to SEQ ID NO: 1 under stringent conditions. Fragments of SEQ ID NO: 1 may be 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99% identical to SEQ ID NO: 1. Fragments of SEQ ID NO: 1 are collected and cloned into expression vectors by standard cloning methods. The expression vectors are transiently transformed into plants either with *Agrobacterium* or biolistic methods.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1

Identification and Design of Epidermal-Specific Expression Cassette for Maize An expression cassette was developed based on the potato chitinase C gene (StChiC) and YPT® technology. To ensure that all the requisite regulatory sequence was captured in the expression cassette, an inclusive design strategy was used.

Figure 1:
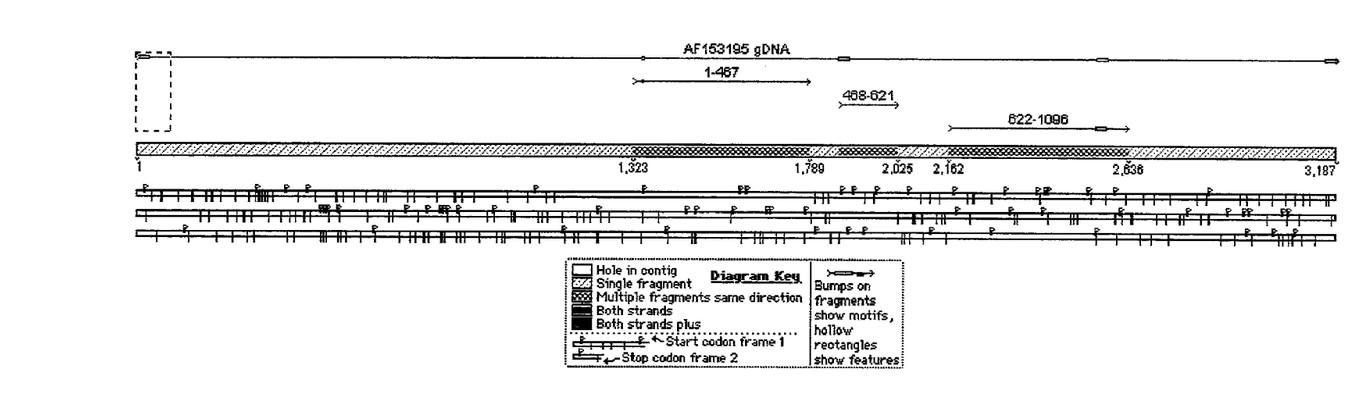
FIG. 1 is a diagram of the annotated StChiC gDNA. The cartoon depicts alignment of the StChiC gDNA with the StChiC cDNA sequence. The cDNA is broken into three exons that are labeled according to bases they represent. Each exon aligns perfectly with the gDNA template and the two introns defined by the alignment are bracketed by GT . . . AG border sequence.

A first step was the base-level annotation of the StChiC gDNA sequence which can be found in GenBank (AF153195) (SEQ ID NO: 3). The StChiC cDNA sequence is SEQ ID NO: 4 in the Sequence Listing. A gene's cDNA sequence can be used to annotate its gDNA sequence. Positions were marked for the translation start and stop codons, introns, exons, 5'-untranscribed and the 3'-untranscribed sequence. By way of example, the gDNA/cDNA alignment and annotation is illustrated in cartoon form in FIG. 1. Three exons and two introns are shown. The exons are labeled according to cDNA base numbers. The gDNA and cDNA sequences align precisely and the intervening sequences (introns) are flanked by GT . . . AG borders. Gaps in between exons represent introns.

An expression cassette was designed that incorporated the promoter (SEQ ID NO: 1) and 637 bp of 3'-sequence (SEQ ID NO: 2). Upstream of the gene of interest, the finished expression cassette comprises the StChiC promoter containing 1305 bp of 5'-non-transcribed sequence (SEQ ID NO: 14), the 81 bp first intron (SEQ ID NO: 15), and 488 bp of 5'-UTR representing exon 1 (SEQ ID NO: 16) and part (SEQ ID NO: 17) of the 5' portion of exon 2 (SEQ ID NO: 20). Downstream of the gene of interest, the expression cassette comprises a terminator sequence (SEQ ID NO: 2) derived from the StChiC gene. SEQ ID NO: 2 comprises 637 bp of the 3'-untranslated sequence that begins just past the translation stop codon. This functions as the transcriptional terminator/polyadenylation signal.

Example 2

Construction of the StChiC-GUS Expression Cassette

The StChiC promoter was amplified from potato gDNA template in an Extensor (ABgene) DNA polymerase reaction. A 50 μL reaction mixture contains 10 μg gDNA, 5 μL 10× Extensor Buffer, 2.0 μL 10 mM dNTP mix, 1.0 μL of 20 μM forward primer STCHICP1 forty (5'-TATATACTCGAGG-GACCCTTTATGTTCATAGTGCACACA-3') (SEQ ID NO: 5), 1.0 μL of 20 μM reverse primer STCHICP2 rev (5'-CTC-CCATGGTTTACTGAAGCCCATCCTCCTA-3') (SEQ ID NO: 6), and 10.0 μL 5×Q solution. The thermocycling program was 95° C. for 2 minutes followed by 40 cycles of 95° C. for 30 seconds, 50° C. for 1 minute, and 68° C. for 4 minutes. The final extension step was 68° C. for 15 minutes. The 1.9 kb reaction product was gel-purified on 1% TBE agarose and the DNA was extracted using Qiaprep DNA extraction method (Qiagen, Cat. No. 27106). The DNA was cloned into a pCR-TOPO® vector (Invitrogen, Cat. No. K4750-20).

The StChiC (*Solanum tuberosum* Chitinase C) promoter was modified in a series of QuikChange®-mediated site-directed mutagenesis reactions using the Stratagene QuikChange Multi-site mutagenesis kit (Stratagene, Cat. No. 200513). Modifications were made to silence the target gene's endogenous translation initiation codons, to introduce STOP codons and to correct point mutations created during amplification. The 25 μL reactions contained 1 μL pCR-TOPO-prStChiC, 2.5 μL 10× QuikChange buffer, 1 μL QuikChange dNTP mix, 0.75 μL Quik solution, 1 μL QuikChange DNA polymerase and 1 μL of 20 μM of at least one of the following forward primer oligonucleotides:

```
                                       (SEQ ID NO: 7)
prStChiCmut1
(5'-GATAGTTATACATTTCAAAAAAAAAAAAACG-3')

(SEQ ID NO: 8)
prStChiCmut2
(5'-CACTGATGACTATTGTGGTCCTGGCAAGTGTC-3')

(SEQ ID NO: 9)
prStChiCmut3.1
(5'-TACTTCTATTAAAAAGAGGCTTTCTGCTTG-3')

(SEQ ID NO: 10)
prStChiCmut4
(5'-TATATATATAGGAGGTTGGGCTTCAGTAAACC-3')

(SEQ ID NO: 11)
prStChiCmut5.1
(5'-GTTGCTTATGCATCGCTAGGAAAATTCTTGTGAAG-3')
```

The thermocycling program was 95° C. for 2 minutes followed by 40 cycles of 95° C. for 1 minute, 50° C. for 1 minute and 65° C. for 15 minutes. The product was processed as described by the manufacturer (Stratagene) and completely sequenced. The StChiC promoter sequence, SEQ ID NO: 1, is shown in the Sequence Listing. The corrected StChiC promoter was excised as an XhoI/NcoI fragment, ligated to a similarly digested pNOV6901 cloning vector, transformed into TOP10 cells (Invitrogen) and sequenced.

The StChiC terminus was amplified from potato gDNA template in an Extensor (ABgene) DNA polymerase reaction. A 50 μL reaction mixture contains 10 μg gDNA, 5 μL 10× Extensor Buffer, 2.0 μL 10 mM dNTP mix, 1.0 μL of 20 μM forward primer STCHICT1 forw (5'-TATATAGAGCT-CAACTTTATCATCTGTTTGTTGT-3') (SEQ ID NO: 12), 1.0 μL of 20 μM reverse primer STCHICT2 rev (5'-TATATACCCGGGCGGTCCGGTAC-CAAAAATTCAAGACTCAAAATCAG-3') (SEQ ID NO: 13), and 10.0 μL 5×Q solution. The thermocycling program was 95° C. for 2 minutes followed by 40 cycles of 95° C. for 30 seconds, 50° C. for 1 minute and 68° C. for 4 minutes. The final extension step was 68° C. for 15 minutes. The 0.6 kb reaction product was gel-purified on 1% TBE agarose and the DNA was extracted using Qiaprep DNA extraction method. The DNA was cloned into a pCR-TOPO vector and sequenced. The sequence data are shown in SEQ ID NO: 2 of the Sequence Listing.

The StChiC terminus was excised as a SacI/XmaI fragment and ligated to a similarly cut pNOV6901-prStChiC vector (see above). This produced the assembly (plant expression) vector 17047 (prStChiC-GUS-tStChiC). The StChiC regulatory sequences are linked to the β-glucuronidase (GUS) reporter gene.

The complete StChiC-GUS expression cassette was mobilized as a SanDI/RsrII fragment into the RsrII site of binary vector 15289, producing the construct, binary vector 17048 (B-prStChiC-GUS-tStChiC-PMI).

Binary vector 17048 was created by the following method: The recipient vector was linearized with the restriction enzyme RsrII. The assembly vector was digested with restriction enzymes RsrII and SanDI, excising the expression cassette. The expression cassette was then ligated to the recipient vector at the RsrII site.

Example 3

Production of T0 Transgenic Maize

The 17048 binary vector was transferred to *Agrobacterium*, then used for maize transformation. The binary vector was transformed into maize by transformation techniques well known to those skilled in the art. Methods for transforming monocots, primarily by use of *Agrobacterium tumefaciens*, and obtaining transgenic plants have been published, including for biolistic transformation in maize (U.S. Pat. No. 6,051,409) and transformation using *Agrobacterium* (U.S. Pat. No. 6,162,965).

Twenty transgenic events were taken to maturity. Each event was genotyped using TAQMAN® (Applied Biosystems) analysis. The TAQMAN® targets were PMI, the GUS gene and a binary vector backbone target (Spectinomycin antibiotic resistance marker, Spec). In addition, leaf tissue from T0 plants was assayed for GUS transcript via qRT-PCR. The T0 event characterization data are summarized in Table 1 below, which shows that GUS was expressed in Events 8, 9, 14, and 16 through 20.

TABLE 1

Event Data

| T0 Plant | Genotype | PMI copy number | Spec copy number | GOI-1 copy number | GOI-2 copy number | qRT-PCR mean | qRT-PCR StDev |
|---|---|---|---|---|---|---|---|
| Event 1 | T0 Self | 0.82 | 0.01 | 0.65 | 0.85 | 0.00 | 0.00 |
| Event 2 | wildtype X T0 | 1.00 | 1.17 | 0.82 | 0.75 | 0.00 | 0.00 |
| Event 3 | T0 Self | 0.85 | 0.00 | 0.74 | 0.82 | 0.00 | 0.00 |
| Event 4 | T0 Self | 0.81 | 0.01 | 0.74 | 0.78 | 0.00 | 0.00 |
| Event 5 | T0 Self | 0.70 | 0.00 | 0.74 | 0.87 | 0.00 | 0.00 |
| Event 6 | wildtype X T0 | 0.95 | 0.00 | 0.00 | 0.00 | 0.00 | 0.00 |
| Event 7 | T0 Self | 0.75 | 0.00 | 0.76 | 0.88 | 0.00 | 0.00 |
| Event 8 | T0 Self | 0.72 | 0.00 | 1.40 | 1.13 | 39.14 | 4.14 |
| Event 9 | wildtype X T0 | 0.89 | 0.00 | 0.89 | 0.94 | 28.76 | 3.33 |
| Event 10 | T0 X wildtype | 0.64 | 0.00 | 0.59 | 0.41 | 0.00 | 0.00 |
| Event 11 | T0 Self | 1.11 | 0.03 | 1.04 | 1.15 | 0.00 | 0.00 |
| Event 12 | T0 Self | 0.68 | 0.01 | 0.80 | 0.76 | 1.55 | 0.44 |
| Event 13 | T0 Self | 0.92 | 0.00 | 0.99 | 0.71 | 0.00 | 0.00 |
| Event 14 | T0 Self | 0.86 | 0.00 | 0.91 | 0.68 | 39.62 | 1.99 |
| Event 15 | T0 Self | 1.00 | 0.00 | 0.99 | 0.89 | 0.00 | 0.00 |
| Event 16 | T0 Self | 0.44 | 0.00 | 0.74 | 0.90 | 30.26 | 2.55 |
| Event 17 | T0 Self | 0.93 | 0.00 | 0.95 | 0.97 | 644.76 | 12.54 |
| Event 18 | T0 Self | 0.58 | 0.00 | 0.74 | 0.84 | 624.19 | 19.74 |
| Event 19 | T0 Self | 0.90 | 0.00 | 0.82 | 0.93 | 315.00 | 16.20 |
| Event 20 | T0 Self | 0.81 | 0.00 | 0.78 | 0.78 | 306.16 | 12.80 |

Each T0 event used plasmid 17048, transformed wildtype maize, Trait Construct StChiC-GUS, selectable marker PMI, and GOI zygosity segregation

Example 4

GUS Analysis in T0 Transgenic Maize

GUS protein accumulation was examined in T0 transgenic maize tissue with a variety of assays. The data are summarized in Table 2. GUS protein was measured directly by ELISA and by enzyme activity assay. GUS protein was detected in plant tissues by histochemical assay. Tissue was incubated in histochemical reagent overnight at 37° C. and cleared with ethanol. The data show that events vary with respect to GUS accumulation. There was a positive correlation between the GUS enzyme activity and the level of GUS protein extracted from similar leaf tissue.

A significant conclusion from this analysis is that the StChiC expression cassette functions to drive GUS protein accumulation in the epidermal cell layer of transgenic maize. Furthermore this expression cassette is capable of modest GUS protein accumulation. All plants were fertile and produced ample seed.

Example 5

GUS Analysis in T1 Transgenic Maize

Events 5, 12, and 14 were selected for T1 analysis. A total of 24 seed were planted for each event. The germination rates were 42, 46 and 88%, respectively. The seedlings were genotyped by zygosity TAQMAN® (Applied Biosystems) assay. Histochemical localization of GUS activity and GUS ELISA were performed on young leaf tissue. Tissue was incubated in histochemical reagent overnight at 37° C. and cleared with ethanol. The data are summarized in Table 3. For events 5 and 12 the GUS expression data track zygosity data quite well. The homozygotes accumulate GUS protein to a significantly higher level compared to hemizygotes. The azygotes (not shown) do not accumulate GUS protein. The correlation is not as high with event 14 seedlings.

TABLE 2 prStChic-driven GUS expression in T0 maize leaf tissue detected by histochemical staining, MUG activity and ELISA assay. GUS MUG activity and ELISA assay are from four independent assays and values are mean ± SE. Construct ID = 17048, Component = cGus-15, and Generation = T0 for all rows.

| Event ID | GUS histochemical staining | MUG activity (pmol/min/mg protein) | GUS ELISA (ng/mg protein) |
|---|---|---|---|
| Event 1 | moderate | 3548.6 ± 705.9 | 347.6 ± 14.7 |
| Event 2 | light | 2443.0 ± 604.2 | 229.2 ± 33.3 |
| Event 3 | moderate | 3091.4 ± 190.1 | 304.4 ± 22.5 |
| Event 4 | moderate | 605.2 ± 333.7 | 86.7 ± 10.9 |
| Event 5 | moderate | 5498.9 ± 881.4 | 481.2 ± 107.7 |
| Event 20 | moderate | 1798.2 ± 561.4 | 183.0 ± 17.8 |
| Event 6 | non-staining | undetectable | undetectable |
| Event 7 | moderate | 3562.2 ± 453.3 | 318.6 ± 103.0 |
| Event 8 | moderate | 3708.1 ± 884.5 | 274.8 ± 53.6 |

TABLE 2-continued prStChic-driven GUS expression in T0 maize leaf tissue detected by histochemical staining, MUG activity and ELISA assay. GUS MUG activity and ELISA assay are from four independent assays and values are mean ± SE. Construct ID = 17048, Component = cGus-15, and Generation = T0 for all rows.

| Event ID | GUS histochemical staining | MUG activity (pmol/min/mg protein) | GUS ELISA (ng/mg protein) |
|---|---|---|---|
| Event 9 | moderate | 2457.6 ± 235.5 | 255.7 ± 39.5 |
| Event 10 | moderate | 4638.7 ± 714.6 | 297.8 ± 56.1 |
| Event 11 | light | 516.1 ± 176.4 | 68.3 ± 24.3 |
| Event 12 | moderate | 4806.1 ± 212.8 | 328.9 ± 44.6 |
| Event 13 | moderate | 2774.9 ± 558.0 | 243.5 ± 47.7 |
| Event 14 | moderate | 6050.4 ± 683.5 | 349.3 ± 51.6 |
| Event 15 | light | 2361.5 ± 724.6 | 204.0 ± 64.1 |
| Event 16 | non-staining | undetectable | 25.1 ± 4.8 |
| Event 17 | very light | undetectable | 43.1 ± 5.9 |
| Event 18 | non-staining | undetectable | 32.2 ± 5.0 |
| Event 19 | light | 1699.6 ± 391.7 | 155.1 ± 59.0 |

TABLE 3 prStChic-driven GUS expression in T1 maize leaf tissue detected by histochemical staining and ELISA assay; For all rows Construct ID = 17048, Component = cGus-15, and Generation = T1

| Sample Id | zygosity | GUS histochemical staining | GUS ELISA (ng/mg protein) |
|---|---|---|---|
| Event 5-2 | Hom | moderate | 965 |
| Event 5-3 | 0 | No-staining | 45 |
| Event 5-6 | Hom | moderate | 1199 |
| Event 5-7 | Het | moderate | 321 |
| Event 5-8 | Het | moderate | 394 |
| Event 5-9 | Hom | light | 421 |
| Event 5-17 | Het | light | 244 |
| Event 5-18 | Het | moderate | 376 |
| Event 5-24 | Het | light | 289 |
| Event 12-14 | Het | moderate | 243 |
| Event 12-18 | Het | moderate | 409 |
| Event 12-22 | Hom | moderate | 1547 |
| Event 12-23 | Hom | moderate | 510 |
| Event 14-3 | Het | moderate | 204 |
| Event 14-4 | Hom | moderate | 1537 |
| Event 14-5 | Hom | moderate | 1811 |
| Event 14-6 | Hom | moderate | 1339 |
| Event 14-8 | Hom | moderate | 1130 |
| Event 14-9 | Het | moderate | 529 |
| Event 14-10 | Het | moderate | 318 |
| Event 14-11 | Hom | moderate | 1116 |
| Event 14-12 | Hom | light | 152 |
| Event 14-13 | Het | light | 326 |
| Event 14-14 | Hom | moderate | 369 |
| Event 14-15 | Het | moderate | 971 |
| Event 14-16 | Het | light | 267 |
| Event 14-17 | Het | moderate | 405 |
| Event 14-18 | Het | light | 484 |
| Event 14-19 | Hom | moderate | 1541 |
| Event 14-20 | Hom | moderate | 1226 |
| Event 14-21 | Hom | moderate | 838 |

Events 5 and 12 illustrate that the GUS protein accumulated in a cell-layer specific manner. One purpose of this expression cassette is to express trait genes in the epidermal cell layer in transgenic maize. The evidence supports that the StChiC expression cassette functions to express GUS protein in the epidermal tissue of transgenic maize.

Example 6

Modifications to Regulatory Sequences

Additional modifications to the modified promoter of SEQ ID NO: 1 are prepared by site directed and/or random mutagenesis and operably linked to a heterologous gene in accordance with techniques disclosed in the Examples herein above. Activity is compared to the activity of SEQ ID NO: 1. Additional techniques can be found in U.S. Pat. No. 7,615,624 to Budworth et al., herein incorporated by reference in its entirety.

REFERENCES

All references listed below, as well as all references cited in the instant disclosure, including but not limited to all patents, patent applications and publications thereof, scientific journal articles, and database entries (e.g., GENBANK® database entries and all annotations available therein) are incorporated herein by reference in their entireties to the extent that they supplement, explain, provide a background for, or teach methodology, techniques, and/or compositions employed herein.

Ancillo, G., et al., Planta 217:566-576 (2003).
Koyama, T., et al., J. Biosci. Bioengineering 99(1): 38-42 (2005).
Liu, Z.-Z., et al., Planta 216: 824-833 (2005).
Wang, Y., et al, Plant Journal: 413-424 (2005).
Ebert et al., Proc. Natl. Acad. Sci. USA 84:5745-5749 (1987)
Lawton et al., Plant Mol. Biol. 9:315-324 (1987)
Odell et al., Nature 313:810-812 (1985)
Sanger et al., Plant Mol. Biol. 14, 43343 (1990)
Pellegrineschi et al., Biochem. Soc. Trans. 23(2):247-250 (1995)
Walker et al., Proc: Natl. Acad. Sci. USA 84:6624-66280 (1987)
Yang et al., Proc. Natl. Acad. Sci. USA 87:414-44148 (1990)
Chandler et al., Plant Cell 1:1175-1183 (1989)
Published U.S. Patent Application No. US 2007/0006344 A1 to Nuccio et al.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. An isolated nucleic acid sequence comprising SEQ ID NO: 1.

2. An expression cassette comprising SEQ ID NO: 1, operably linked to a heterologous gene.

3. The expression cassette of claim 2, further comprising SEQ ID NO: 2.

4. The expression cassette of claim 2 further comprising a eukaryotic gene regulatory sequence.

5. The expression cassette of claim 2 wherein the heterologous gene is a gene for resistance to herbicides, pests, disease, or drought.

6. A plant, plant tissue, or plant cell comprising the expression cassette of claim 2.

7. The plant, plant tissue, or plant cell of claim 6, wherein the plant, plant cell, or plant tissue is monocotyledonous.

8. The plant, plant tissue, or plant cell of claim 7, wherein the plant, plant cell, or plant tissue is a maize plant, plant cell, or plant tissue.

9. A method of expressing a heterologous gene comprising:
   a. providing an expression cassette comprising SEQ ID NO: 1, operably linked to a heterologous gene, wherein the expression cassette is functional in a plant, plant tissue, or plant cell;
   b. introducing said expression cassette into a suitable vector for plant transformation;
   c. transforming vector into a plant, plant tissue, or plant cell; and
   d. creating a plant, plant tissue, or plant cell comprising the expression cassette, wherein the heterologous gene is expressed.

10. The method of claim 9 wherein the heterologous gene is expressed in an epidermal cell layer of aerial plant tissue.

11. The method of claim 9, wherein the plant, plant tissue, or plant cell, or a portion thereof is monocotyledonous.

12. The method of claim 11, wherein the plant, plant tissue, plant cell, or a portion thereof is a maize plant, plant tissue, plant cell, or portion thereof.

13. A plant, plant tissue, or plant cell, made by the method of claim 9, or a portion thereof comprising the expression cassette.

14. A progeny, seed, or grain produced by the plant, plant tissue, plant cell, or portion thereof of claim 13, wherein the progeny, seed, or grain comprises the expression cassette.

* * * * *

SEQUENCE LISTING

<160> NUMBER OF SEQ ID NOS: 18

<210> SEQ ID NO 1
<211> LENGTH: 1874
<212> TYPE: DNA
<213> ORGANISM: Solanum tuberosum

```
<220> FEATURE:
<221> NAME/KEY: misc_feature
<222> LOCATION: (1)..(1874)
<223> OTHER INFORMATION: StChiC 5' regulatory sequence engineered
<220> FEATURE:
<221> NAME/KEY: misc_feature
<222> LOCATION: (1)..(1305)
<223> OTHER INFORMATION: 5' nontranscribed sequence engineered
<220> FEATURE:
<221> NAME/KEY: misc_feature
<222> LOCATION: (1306)..(1772)
<223> OTHER INFORMATION: Exon 1 engineered
<220> FEATURE:
<221> NAME/KEY: misc_feature
<222> LOCATION: (1773)..(1853)
<223> OTHER INFORMATION: Intron 1
<220> FEATURE:
<221> NAME/KEY: misc_feature
<222> LOCATION: (1854)..(1874)
<223> OTHER INFORMATION: Partial exon 2 engineered
<220> FEATURE:
<221> NAME/KEY: misc_feature
<222> LOCATION: (1869)..(1874)
<223> OTHER INFORMATION: Added Kozak sequence

<400> SEQUENCE: 1 cccttttatgt tcatagtgca cacaaaataa gtttgtcaat ttaaagagtt ttgatagtta      60
tacatttcaa aaaaaaaaaa aacgtgggaa gttattttgt aaaacaaact ggtatggtta     120 tatttttta attgactata aaggaaaca aaaaacttaa actacctat atattgaatt         180 ttaaattgaa attaactgtt tgaaaatttt acataattat ccaaatttt aaaactgcaa      240 aaatttaatt gactattaaa tttgttttgt ttgaaattaa ctgattttta aaaataatt       300 aaatagatgt cataataaag ataagtattc tgattctgat taggacaaaa ataagagtcc     360
aaaaatcata taaacatcag tcacatgtat agtcagttaa ttattttaa aataaaataa     420 ttcaaattat tattgataaa gatggctata agagaatat ttttttaaaa aaaaacatga      480 aataatggt aaaaatgtga gagaaggctt ccattaataa tatgatttga ttgaataaaa     540
aattaagaaa gagaaaatca atatatagaa aaacaaagta cgtaaaagag caaaactgtg    600
attgaaaaag tcaaaaaaat gtaaacaata attatcaatc ccataaaatt agcacataag    660
gacaaaaata agagtccaaa aatcatataa acatcagtca catgtatagt cagttaatta    720
tttttaagat aaaataattc aaattattat tgataaagat ggctataaag agaatatttt    780
tttttaaaaa aacatgaaa ataatggtaa aaatgtgaga gaaggcttcc attaataata     840
tgatttgatt gaataaaaaa ttaagagaga gaaaatcaat atatagaaaa acaaagtacg    900
taaaagagca aaactgtggt tgacaagtca aaaaatgta aacaataatt atcaatccca     960
taaaattagc ataaaccttt ccctaaaaaa ggtaatagat acggatacca actttattt    1020 taacaaataa aaaattaaat attttgttat gtttgtaatt aaaaacttag ttctgtaaat   1080 aaaaagagt atattcttgt aattttccta ttcaaatata acatgtaaaa gtgcacggac    1140
aaggtatttt tttaatctag ataacagccg ccggttagca gaggtggccc caataaaaca   1200
gatactccct attaatgaga aattgagaat tgtgtcttgt ttagtcaaca tctgctttgt   1260
caccctcctt gcctataaat acctctactt caccactctc ttcccatcac ttattactac   1320
ttctattaaa aagaggcttt ctgcttgttc cttacttttt tctctcttat tgttaactgt   1380
ctcggcagaa caatgtggta ggcaggcagg aggtgcgcct tgtgccgcgg gactctgttg   1440
cagcaatgtt ggctggtgtg gtaacactga tgactattgt ggtcctggca agtgtcaaag   1500
ccagtgtcct tctggtcctt ctcccaaacc acctacccct ggccctggtc cttctggtgg   1560
agacataggc gatgtcatct caaattccat gtttgatcag ttgcttatgc atcgctagga   1620
```

-continued

```
aaaattcttgt gaaggaaaga ataatttcta tagttacaat gcattcatca atgctgccag    1680
gttttttagt ggctttggca ctactggtga taccactgcc cgaaaaaagg aaattgctgc    1740
tttctttgcc caaacctccc atgaaactac tggtacgttg attcgaattt gatggattca    1800
acttttcaat tgagatctaa tataattgat tatgtaccta tttatatata taggaggttg    1860
ggcttcagta aacc                                                       1874
```

<210> SEQ ID NO 2
<211> LENGTH: 637
<212> TYPE: DNA
<213> ORGANISM: Solanum tuberosum
<220> FEATURE:
<221> NAME/KEY: misc_feature
<222> LOCATION: (1)..(637)
<223> OTHER INFORMATION: StChiC terminator sequence
<220> FEATURE:
<221> NAME/KEY: misc_feature
<222> LOCATION: (1)..(81)
<223> OTHER INFORMATION: 3'-untranslated sequence
<220> FEATURE:
<221> NAME/KEY: misc_feature
<222> LOCATION: (82)..(637)
<223> OTHER INFORMATION: 3'-nontranscribed sequence

<400> SEQUENCE: 2

```
caactttatc atctgtttgt tgtagtctct tgcggaccca actatgaata aatttactta      60
tgtaattgtg ttgtaatcgt ctttcatttt aataaacaaa gactttgtcc acgatagtgg    120
atagttctac ttctacagct gtgacttgtg acaggtagct ggttcaattc gaaaccagat    180
aaatattgac tagtcaatcg agccatctca ttatttagaa aaggatttaa gttattatgg    240
gttcacctac ccactcgact tttaattaca ataatcaag  atttgctaat tgatgaagtt    300
catcacatac aaatcgggca agttggttga ataccaaaac aaacatgccc aaggcccgac    360
taatccaaat tcgtcttgaa agaaaaatgc attatgacat gttttgtctt taacaaacct    420
cctacagctt gtaattgcac gtattactgg ttaatctcag tcatttgatg agacaacttc    480
tcttctaagt tttatgagat ttaagtgaat gaaaaccttc ctagatgata catatttta    540 aaaattagtt gaaagaaaga agaactttga acctcaaaaa ttaggcatcc aaggtacagc    600
caccgtctct gattttgagt cttgaatttt tggtacc                             637
```

<210> SEQ ID NO 3
<211> LENGTH: 3187
<212> TYPE: DNA
<213> ORGANISM: Solanum tuberosum
<220> FEATURE:
<221> NAME/KEY: misc_feature
<222> LOCATION: (1)..(3187)
<223> OTHER INFORMATION: gDNA

<400> SEQUENCE: 3

```
aagcttttt ttcccttat gttcatagtg cacacaaaat aagtttgtca atttaaagag       60
ttttgatagt tatacatttc aaaaaaaaaa aaaacgtggg aagttatttt gtaaaacaaa    120
ctggtatggt tatattttt taattgacta taaaaggaaa caaaaaactt aaactacctt    180
atatattgaa ttttaaattg aaattaactg tttgaaaatt ttacataatt atccaaattt    240
ttaaaactgc aaaaatttaa ttgactatta aatttgtttt gtttgaaatt aactgatttt    300
taaaaaataa ttaaatagat gtcataataa agataagtat tctgattctg attaggacaa    360
aaataagagt ccaaaaatca tataaacatc agtcacatgt atagtcagtt aattattttt    420
aaaataaaat aattcaaatt attattgata aagatggcta taaagagaat atttttttaa    480
```

```
aaaaaaacac atgaaaataa tggtaaaaat gtgagagaag gcttccatta ataatatgat    540
ttgattgaat aaaaaattaa gaaagagaaa atcaatatat agaaaaacaa agtacgtaaa    600
agagcaaaac tgtgattgaa aaagtcaaaa aaatgtaaac aataattatc aatcccataa    660
aattagcaca taaggacaaa ataagagtc caaaaatcat ataaacatca gtcacatgta     720
tagtcagtta attatttta agataaaata attcaaatta ttattgataa agatggctat     780
aaagagaata ttttttttta aaaaaaacat gaaaataatg gtaaaaatgt gagagaaggc    840
ttccattaat aatatgattt gattgaataa aaaattaaga gagagaaaat caatatatag    900
aaaaacaaag tacgtaaaag agcaaaactg tggttgacaa gtcaaaaaaa tgtaaacaat    960
aattatcaat cccataaaat tagcacataa ccttccctaa aaaaggtaat agatacggat   1020
accaacttta tttttaacaa ataaaaaatt aaatatttg ttatgtttgt aattaaaaac    1080
ttagttctgt aaataaaaaa gagtatattc ttgtaatttt cctattcaaa tataacatgt   1140
aaaagtgcac ggacaaggta ttttttttaat ctagataaca gccgccggtt agcagaggtg  1200
gccccaataa aacagatact ccctattaat gagaaattga gaattggtgg tccttgttta   1260
gtcaacatct gctttgtcac cctccttgcc tataaatacc tctacttcac cactctcttc   1320
ccatcactta ttactacttc tattaaaatg aggctttctg cttgttcctt acttttttct   1380
ctcttattgt taactgtctc ggcagaacaa tgtggtaggc aggcaggagg tgcgccttgt   1440
gccgcgggac tctgttgcag caatgttggc tggtgtggta acactgatga ctattgtggt   1500
cctggcaagt gtcaaagcca gtgtccttct ggtccttctc ccaaaccacc tacccctggc   1560
cctggtcctt ctggtggaga cataggcgat gtcatctcaa attccatgtt tgatcagttg   1620
cttatgcatc gcaacgaaaa ttcttgtgaa ggaaagaata atttctatag ttacaatgca   1680
ttcatcaatg ctgccaggtt ttttagtggc tttggcacta ctggtgatac cactgcccga   1740
aaaaaggaaa ttgctgcttt ctttgcccaa acctcccatg aaactactgg tacgttgatt   1800
cgaatttgat ggattcaact tttcaattga gatctaatat aattgattag tgtacctatt   1860
tatatatata ggaggatggg cttcagcacc aaatggacca tacgcatggg gttactgctt   1920
cattacagaa caaaatgacc agagcgatca ctgtacacca agtaatcaat ggccttgtgc   1980
tcctggaagg aaatatttcg gacgaggccc catccaaatt tcacagtaag ttaccataat   2040
tttagcagag tcatggctaa gaattttaata gtaaccaatt ttggctaaat aagtaagggg   2100
aattatttgt tatgaatttt gttgggtcta attacgtgaa ttttaacatt aattaacaca   2160
gcaactacaa ctatgggcca tgtggaagag ccatcgaagt ggacctttta aacaatcctg   2220
atttagtagc cacagattca gttatctcat tcaaatcagc tatctggttc tggatgaccc   2280
ctcaatcacc aaagccttct tgccacgatg tcatcactgg aagatggcaa ccatctgacg   2340
ctgacagagc agccaatcgc ctccctggat tcggtgtcat cacaaacatc atcaatggtg   2400
gcatagaatg tggtcatggc aatgacacca gggtccagga tcgaattggg ttcttcagaa   2460
ggtattgcga aattcttgga gttagtcttg gtgacaatct tgattgtggc aaccagagtc   2520
cttttggaaa tggactctta gtcgattcta tgtaacaact ttatcatctg tttgttgtag   2580
tctcttgcgg acccaactat gaataaattt acttatgtaa ttgtgttgta atcgtctttc   2640 atttttaataa acaaagactt tgtccacgat agtggatagt tctacttcta cagctgtgac   2700
ttgtgacagg tagctggttc aattcgaaac cagataaata ttgactagtc aatcgagcca   2760
tctcattatt tagaaaagga tttaagttat tatgggttca cctacccact cgacttttaa   2820
ttacaaataa tcaagatttg ctaattgatg aagttcatca catacaaatc gggcaagttg   2880
```

-continued

```
gttgaatacc aaaacaaaca tgcccaaggc ccgactaatc caaattcgtc ttgaaagaaa    2940
aatgcattat gacatgtttg ctttaacaaa ctctacagct tataattgca cgattactgg    3000
ttaatctcag tcatttgatg agacaacttc tcttctaagt tttatgagat taagtgaat     3060 gaaaaccttc ctagatgata catatttta aaaattagtt gaaagaaaga agaactttga     3120
acctcaaaaa ttaggcatcc aaggtacagc caccgtctct gattttgagt cttgaatttt    3180
tggtacc                                                              3187
```

```
<210> SEQ ID NO 4
<211> LENGTH: 1096
<212> TYPE: DNA
<213> ORGANISM: Solanum tuberosum
<220> FEATURE:
<221> NAME/KEY: misc_feature
<222> LOCATION: (1)..(1096)
<223> OTHER INFORMATION: cDNA

<400> SEQUENCE: 4
atcacttatt actacttcta ttaaaatgag gctttctgct tgttccttac ttttttctct      60
cttattgtta actgtctcgg cagaacaatg tggtaggcag gcaggaggtg cgccttgtgc    120
cgcgggactc tgttgcagca atgttggctg gtgtggtaac actgatgact attgtggtcc    180
tggcaagtgt caaagccagt gtccttctgg tccttctccc aaaccaccta ccctggccc     240 tggtccttct ggtggagaca taggcgatgt catctcaaat tccatgtttg atcagttgct    300
tatgcatcgc aacgaaaatt cttgtgaagg aaagaataat ttctatagtt acaatgcatt    360
catcaatgct gccaggtttt ttagtggctt tggcactact ggtgatacca ctgcccgaaa    420
aaaggaaatt gctgctttct ttgcccaaac ctcccatgaa actactggag atgggcttc     480 agcaccaaat ggaccatacg catggggtta ctgcttcatt acagaacaaa atgaccagag    540
cgatcactgt acaccaagta atcaatggcc ttgtgctcct ggaaggaaat atttcggacg    600
aggccccatc caaatttcac acaactacaa ctatgggcca tgtggaagag ccatcgaagt    660 ggaccttta aacaatcctg atttagtagc cacagattca gttatctcat tcaaatcagc    720
tatctggttc tggatgaccc ctcaatcacc aaagccttct tgccacgatg tcatcactgg    780
aagatggcaa ccatctgacg ctgacagagc agccaatcgc ctccctggat tcggtgtcat    840
cacaaacatc atcaatggtg gcatagaatg tggtcatggc aatgcaccca gggtccagga    900
tcgaattggg ttcttcagaa ggtattgcga aattcttgga gttagtcttg gtgacaatct    960
tgattgtggc aaccagagtc ctttggaaa tggactctta gtcgattcta tgtaacaact    1020
ttatcatctg tttgttgtag tctcttgcgg acccaactat gaataaattt acttatgtaa    1080
ttgtgttgta atcgtc                                                   1096
```

```
<210> SEQ ID NO 5
<211> LENGTH: 39
<212> TYPE: DNA
<213> ORGANISM: Artificial Sequence
<220> FEATURE:
<223> OTHER INFORMATION: Artificial PCR forward primer, STCHICP1 forw,
      used to clone the 5' regulatory sequence of STCHIC

<400> SEQUENCE: 5
tatatactcg agggaccctt tatgttcata gtgcacaca                              39
```

```
<210> SEQ ID NO 6
<211> LENGTH: 31
<212> TYPE: DNA
<213> ORGANISM: Artificial Sequence
```

-continued

```
<220> FEATURE:
<223> OTHER INFORMATION: Artificial PCR reverse primer, STCHICP2 rev,
      used to clone the 5' regulatory sequence of STCHIC

<400> SEQUENCE: 6
ctcccatggt ttactgaagc ccatcctcct a                              31

<210> SEQ ID NO 7
<211> LENGTH: 32
<212> TYPE: DNA
<213> ORGANISM: Artificial Sequence
<220> FEATURE:
<223> OTHER INFORMATION: Artificial PCR mutagenic primer prStChiCmut1

<400> SEQUENCE: 7
gatagttata catttcaaaa aaaaaaaaaa cg                             32

<210> SEQ ID NO 8
<211> LENGTH: 32
<212> TYPE: DNA
<213> ORGANISM: Artificial Sequence
<220> FEATURE:
<223> OTHER INFORMATION: Artificial PCR mutagenic primer prStChiCmut2

<400> SEQUENCE: 8
cactgatgac tattgtggtc ctggcaagtg tc                             32

<210> SEQ ID NO 9
<211> LENGTH: 30
<212> TYPE: DNA
<213> ORGANISM: Artificial Sequence
<220> FEATURE:
<223> OTHER INFORMATION: Artificial PCR mutagenic primer prStChiCmut3.1

<400> SEQUENCE: 9
tacttctatt aaaagaggc tttctgcttg                                 30

<210> SEQ ID NO 10
<211> LENGTH: 32
<212> TYPE: DNA
<213> ORGANISM: Artificial Sequence
<220> FEATURE:
<223> OTHER INFORMATION: Artificial PCR mutagenic primer prStChiCmut4

<400> SEQUENCE: 10
tatatatata ggaggttggg cttcagtaaa cc                             32

<210> SEQ ID NO 11
<211> LENGTH: 35
<212> TYPE: DNA
<213> ORGANISM: Artificial Sequence
<220> FEATURE:
<223> OTHER INFORMATION: Artificial PCR mutagenic primer prStChiCmut5.1

<400> SEQUENCE: 11
gttgcttatg catcgctagg aaaattcttg tgaag                          35

<210> SEQ ID NO 12
<211> LENGTH: 34
<212> TYPE: DNA
<213> ORGANISM: Artificial Sequence
<220> FEATURE:
<223> OTHER INFORMATION: Artificial PCR forward primer, STCHICT1 forw,
      used to clone the 3' regulatory sequence of STCHIC

<400> SEQUENCE: 12
tatatagagc tcaactttat catctgtttg ttgt                           34
```

```
<210> SEQ ID NO 13
<211> LENGTH: 47
<212> TYPE: DNA
<213> ORGANISM: Artificial Sequence
<220> FEATURE:
<223> OTHER INFORMATION: Artificial PCR reverse primer, STCHICT2 rev,
      used to clone the 3' regulatory sequence of STCHIC

<400> SEQUENCE: 13
tatatacccg ggcggtccgg taccaaaaat tcaagactca aaatcag              47

<210> SEQ ID NO 14
<211> LENGTH: 1305
<212> TYPE: DNA
<213> ORGANISM: Solanum tuberosum
<220> FEATURE:
<221> NAME/KEY: misc_feature
<222> LOCATION: (1)..(1305)
<223> OTHER INFORMATION: 5'-nontranscribed sequence engineered

<400> SEQUENCE: 14
ccctttatgt tcatagtgca cacaaaataa gtttgtcaat ttaaagagtt ttgatagtta      60
tacatttcaa aaaaaaaaaa aacgtgggaa gttattttgt aaaacaaact ggtatggtta    120
tattttttta attgactata aaaggaaaca aaaaacttaa actaccttat atattgaatt    180
ttaaattgaa attaactgtt tgaaaatttt acataattat ccaattttt  aaaactgcaa    240 aaatttaatt gactattaaa tttgttttgt ttgaaattaa ctgattttta aaaaataatt    300
aaatagatgt cataataaag ataagtattc tgattctgat taggacaaaa ataagagtcc    360
aaaaatcata taaacatcag tcacatgtat agtcagttaa ttatttttaa aataaaataa    420
ttcaaattat tattgataaa gatggctata aagagaatat ttttttaaaa aaaaacatga    480
aaataatggt aaaaatgtga gagaaggctt ccattaataa tatgatttga ttgaataaaa    540
aattaagaaa gagaaaatca atatatagaa aaacaaagta cgtaaaagag caaaactgtg    600
attgaaaaag tcaaaaaaat gtaaacaata attatcaatc ccataaaatt agcacataag    660
gacaaaaata agagtccaaa aatcatataa acatcagtca catgtatagt cagttaatta    720
tttttaagat aaaataattc aaattattat tgataaagat ggctataaag agaatatttt    780
ttttaaaaaa aaacatgaaa ataatggtaa aaatgtgaga gaaggcttcc attaataata    840
tgatttgatt gaataaaaaa ttaagagaga gaaaatcaat atatagaaaa acaaagtacg    900
taaaagagca aaactgtggt tgacaagtca aaaaaatgta aacaataatt atcaatccca    960
taaaattagc ataaccctt  ccctaaaaaa ggtaatagat acggatacca actttattt   1020 taacaaataa aaaattaaat attttgttat gtttgtaatt aaaaacttag ttctgtaaat   1080
aaaaaagagt atattcttgt aattttccta ttcaaatata acatgtaaaa gtgcacggac   1140
aaggtatttt tttaatctag ataacagccg ccgttagca  gaggtggccc caataaaaca   1200
gatactccct attaatgaga aattgagaat tgtgtcttgt ttagtcaaca tctgctttgt   1260
caccctcctt gcctataaat acctctactt caccactctc ttccc                 1305

<210> SEQ ID NO 15
<211> LENGTH: 81
<212> TYPE: DNA
<213> ORGANISM: Solanum tuberosum
<220> FEATURE:
<221> NAME/KEY: intron 1
<222> LOCATION: (1)..(81)
```

-continued

```
<400> SEQUENCE: 15
gtacgttgat tcgaatttga tggattcaac ttttcaattg agatctaata taattgatta      60
tgtacctatt tatatatata g                                                81

<210> SEQ ID NO 16
<211> LENGTH: 467
<212> TYPE: DNA
<213> ORGANISM: Solanum tuberosum
<220> FEATURE:
<221> NAME/KEY: misc_feature
<222> LOCATION: (1)..(467)
<223> OTHER INFORMATION: exon 1 engineered

<400> SEQUENCE: 16
atcacttatt actacttcta ttaaaaagag gctttctgct tgttccttac tttttctct       60 cttattgtta actgtctcgg cagaacaatg tggtaggcag gcaggaggtg cgccttgtgc     120
cgcgggactc tgttgcagca atgttggctg gtgtggtaac actgatgact attgtggtcc    180
tggcaagtgt caaagccagt gtccttctgg tccttctccc aaaccaccta ccctggccc     240 tggtccttct ggtggagaca taggcgatgt catctcaaat tccatgtttg atcagttgct    300
tatgcatcgc taggaaaatt cttgtgaagg aaagaataat ttctatagtt acaatgcatt    360
catcaatgct gccaggtttt ttagtggctt tggcactact ggtgatacca ctgcccgaaa   420
aaaggaaatt gctgctttct ttgcccaaac ctcccatgaa actactg                 467

<210> SEQ ID NO 17
<211> LENGTH: 21
<212> TYPE: DNA
<213> ORGANISM: Solanum tuberosum
<220> FEATURE:
<221> NAME/KEY: misc_feature
<222> LOCATION: (1)..(21)
<223> OTHER INFORMATION: partial exon 2 engineered
<220> FEATURE:
<221> NAME/KEY: misc_feature
<222> LOCATION: (16)..(21)
<223> OTHER INFORMATION: Added Kozak sequence

<400> SEQUENCE: 17
gaggttgggc ttcagtaaac c                                                21

<210> SEQ ID NO 18
<211> LENGTH: 154
<212> TYPE: DNA
<213> ORGANISM: Solanum tuberosum
<220> FEATURE:
<221> NAME/KEY: exon 2
<222> LOCATION: (1)..(154)

<400> SEQUENCE: 18
gaggatgggc ttcagcacca aatggaccat acgcatgggg ttactgcttc attacagaac      60
aaaatgacca gagcgatcac tgtacaccaa gtaatcaatg gccttgtgct cctggaagga    120
aatatttcgg acgaggcccc atccaaattt caca                                 154
```